(12) United States Patent
Memic et al.

(10) Patent No.: US 10,881,760 B1
(45) Date of Patent: Jan. 5, 2021

(54) ANTIOXIDANT, ANTIBACTERIAL, INJECTABLE LIGNIN-GELATIN COMPOSITE CRYOGELS FOR WOUND HEALING AND TISSUE ENGINEERING

(71) Applicant: King Abdulaziz University, Jeddah (SA)

(72) Inventors: Adnan Memic, Jeddah (SA); Tuerdimaimaiti Abudula, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 16/989,088

(22) Filed: Aug. 10, 2020

(51) Int. Cl.
*A61L 27/22* (2006.01)
*A61L 27/02* (2006.01)
*A61L 27/56* (2006.01)
*A61L 27/24* (2006.01)
*A61L 27/52* (2006.01)

(52) U.S. Cl.
CPC ........... *A61L 27/222* (2013.01); *A61L 27/025* (2013.01); *A61L 27/24* (2013.01); *A61L 27/52* (2013.01); *A61L 27/56* (2013.01); *A61L 2400/12* (2013.01)

(58) Field of Classification Search
CPC ........ A61L 27/222; A61L 27/56; A61L 27/52; A61L 27/025; A61L 27/24; A61L 2400/12
See application file for complete search history.

(56) References Cited

U.S. PATENT DOCUMENTS

2011/0262489 A1* 10/2011 Zhao .................... A61K 9/0021
424/400

OTHER PUBLICATIONS

Ivanov et al., J. Environmental Chem. Eng. 4 (2016) 1432-1441 (Year: 2016).*

* cited by examiner

*Primary Examiner* — Robert S Cabral
(74) *Attorney, Agent, or Firm* — W&C IP

(57) ABSTRACT

A cryogel which includes lignin nanoparticles embedded in crosslinked gelatin. The cryogel is formed at subfreezing temperatures where aggregation of polymerized or crosslinked materials is prevented by ice crystals. When thawed, the cryogel is a densely crosslinked microporous composition with a plurality of pores ranging from 50-150 μm in size. The cryogel combines a natural bio waste polymer in the form of lignin together with a collagen derived natural polymer. Incorporation of lignin within gelatin improves the mechanical performance of the cryogel and enhances its shape recovery rate. The macropororous composition inhibits growth of both gram positive and gram negative bacteria. In addition, the macoporous composition exhibits excellent free radical scavenging activity. All of the properties make the cryogel an excellent material for wound healing and tissue engineering applications.

13 Claims, 6 Drawing Sheets
(6 of 6 Drawing Sheet(s) Filed in Color)

ANTIOXIDANT, ANTIBACTERIAL, INJECTABLE LIGNIN-GELATIN COMPOSITE CRYOGELS FOR WOUND HEALING AND TISSUE ENGINEERING

FIELD OF THE INVENTION

The invention is related to wound healing and tissue engineering and particularly to a cryogel formulation of natural products which exhibits antioxidant and antibacterial activity such that healing can be achieved with or without antibiotics and other healing agents. In particular, the invention pertains to a cryogel composition that can be injected with a syringe, which recovers its shape, and which can be combined with other treatment agents such as silver or copper oxide nanoparticles.

BACKGROUND

Natural polymer based hydrogels have become one of the most compelling biomaterials for numerous medical applications, including tissue engineering, and wound healing. This is due to their outstanding biocompatibility, and structural, physio-chemical and mechanical similarity with a number of soft tissues in the human body. Swellability of the hydrogels enables them to abundantly adsorb blood and other exudates, while maintaining a comfortable environment for cell and tissue growth.

Recent studies showed physical and structural properties of the hydrogels can be greatly advanced by performing the gelation. These new type of hydrogels are called cryogels, and they possess many exceptional features, such as highly interconnected macroporus structure, remarkable shape-memory property and injectability. Interconnected macropores in the cryogels could facilitate cell migration, provide a convenient access for oxygen and nutrition delivery, and prevent moist aggregation. Moreover, the shape-memory property and injectability allow the cryogels to be delivered to a defected site in a minimally invasive manner via syringe. Applications of cryogels in tissue engineering and wound healing have been described in U.S. Pat. No. 10,045,947B2, US20110262489A1, WO02019048697A1, and WO2017040629A1, each of which is herein incorporated by reference.

A critical issue that has to be overcome in tissue engineering and wound healing is excessive generation of reactive oxygen species (ROS) in the defected and inflammatory tissues. Over formation of ROS can cause a high level of oxidative stress and cellular malfunction. This can lead to substantial damages to critical components of the cells such as nucleic acids, proteins and lipids, and lead to a series of diseases. Thus, it would be advantageous to have biomaterials with an antioxidant property that have a great value in wound healing and tissue engineering applications because they would alleviate oxidative stress in tissue microenvironments. The role of antioxidant biomaterials in tissue engineering and wound healing has been discussed in CA2529413C, AU2009319881B2, U.S. Pat. Nos. 5,667, 501A and 10,143,771B2, each of which is herein incorporated by reference. However, these biomaterials were made by incorporation of synthetic antioxidants, and their usage has been related to numerous health issues. A number of studies suggested that long-term intake of the synthetic antioxidants could cause skin allergies, gastrointestinal tract problems and in some cases increases in the risk of cancer.

Additionally, most surgical prosthesis suffer from an invasion of microbial pathogens, such as *Staphylococcus aureus* (*S. aureus*), *Escherichia coli* (*E. coli*) and *Candida albicans* (*C. albicans*). Bacterial infections must be effectively controlled to avoid their destructive effects, such as suppressing tissue growth, deceleration of surgical recovery and raising complication risks, which even leads to death. Incorporation of antibiotics is one of the most common approaches to prevent implantation-related bacterial infection (see, U.S. Pat. No. 6,475,516B2, JP2015061927A, each of which is herein incorporated by reference). Nevertheless, a continuous usage of antibiotics often results in bacterial resistance due to mutation of bacterial microorganisms. Therefore, it would be advantageous to have biomaterials with intrinsic antibacterial activity, as they would provide a sustainable bacterial inhibition without or minimal side effects.

SUMMARY

One aspect of the invention is to provide a new cryogel formulation which has inherent, antibacterial and antioxidant properties.

Another aspect of the invention is to provide a method of making a cryogel formulation suitable for use in wound healing and tissue engineering applications. The new cryogel formulation may be deposited directly in a wound using a syringe or catheter. Due to its shape recovery properties, the cryogel may expand and fill odd shaped wounds. The cryogel formulation may also be applied on wound sites together with a bandage or other support. In addition, the cryogel can serve as scaffolding for cells in tissue engineering applications.

According to the invention, the cryogel formulation can be prepared by dispersing lignin particles in gelatin. This dispersion then forms a cryogel by storing it at freezing temperatures. The freezing temperatures allow ice crystals to grow. After a suitable storage time, the cryogel formulation is permitted to thaw. Thawing results in a heavily crosslinked cryogel with a number of macropores therein (e.g., on the order of 50-150 μm in size). There is a chemical crosslinker glutaraldehyde that reacts with gelatin to form the thick polymer walls at the phase interface of frozen ice crystals and polymers.

DESCRIPTION OF THE DRAWINGS

The patent or application file contains at least one drawing executed in color. Copies of this patent or patent application publication with color drawings will be provided by the Office upon request and payment of the necessary fee.

DESCRIPTION

Figure 1:
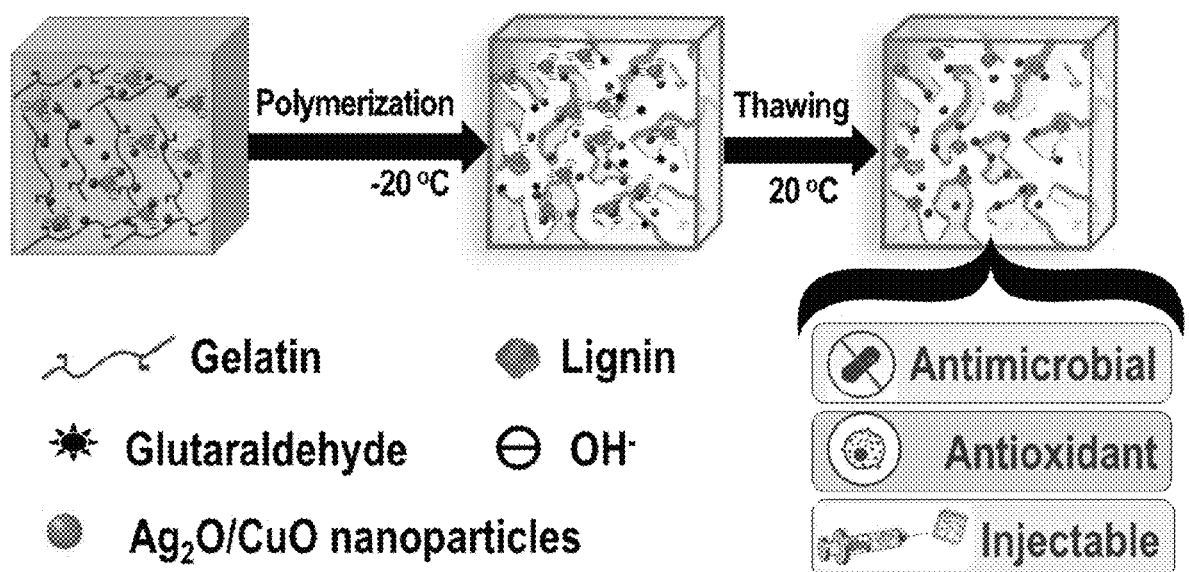
FIG. 1 illustrates overall nanocomposite cryogel formulation using lignin, gelatin and $Ag_2O$/CuO nanoparticles, which possess antimicrobial, antioxidant properties and injectability.

In embodiments of the invention, a lignin-gelatin composite cryogel is produced for use in wound healing or tissue engineering applications. In the composite cyrogel, the lignin acts as antioxidant and an antimicrobial substance. Lignin is a plant-derived natural biopolymer with a complex chemical structure in which hydroxyl and methoxyl functional groups can terminate oxidation propagation reactions. In addition, a number of microorganisms can be inhibited by lignin due to presence of a double bond in the $C\alpha = C_\beta$ position of the side chain and a methyl group in the γ-position. Lignin is typically regarded as a waste product and is readily available.

In some embodiments, the composite cryogels also comprise one or more of silver oxide or copper oxide nanoparticles to improve the antimicrobial properties. These particles can be added through in-situ synthesis during the cryogel formation.

Cryogels are a special type of hydrogels, in which the aggregation of polymerized or cross-linked materials is prevented by ice crystals. Subsequently they show extraordinary features including macroporus structure, self healing properties, flexibility, and injectability. The cryogels described herein are mechanically robust, injectable, biodegradable and biocompatible. Thus, the composite cryogels can be used as wound dressing materials, including for use in chronic wound dressings, or as scaffolds for various tissue engineering applications, particularly in situations where oxidative stress and infection are a special concern.

Over the last several decades, wound healing has been one of the primary concerns in clinics, due to frequent occurrence of burns and traumatic injury, rapid growth of chronic wounds such as diabetic ulcer, and aging population. Wound dressing materials are essential for effective wound treatment, as they protect wounds from external contaminants and second injury, and facilitate skin regeneration. Traditional wound dressings such as dry gauze, foam dressings, and film dressings generally exhibit a passive and slow would healing, and are not suitable to treat large wounds and chronic wounds. Additionally, it is vital to control other diseases followed by dermal wounds such as infection, and conventional drug administration could potentially cause systematic deleterious side effects. Therefore, most of the current research strategy is focused on developing novel bioactive dressing materials with improved functionality. A particular advantage of the present invention is that the cryogel composition exhibits accelerated wound repair advantages without depending on using antibiotics or other related drugs.

Recently, natural polymer based hydrogels being used as wound dressing materials have been extensively explored, due to their tunable physical properties, excellent biocompatibility and structural resemblance of native human tissue. The super hydrophilic nature of the hydrogels allows them to abundantly adsorb blood and other exudates, and they maintain a good humid environment at the wound site. Cryogels are a special type of hydrogels, in which gelation occurs at subzero temperature. They exhibit many unique properties including highly interconnected macroporous structure, remarkable shape-memory and injectability. The macroporous structure of the cryogels may facilitate cell migration, facilitate oxygen and nutrition delivery, and avert moist aggregation in the wound site. The shape-memory property and injectability allow the cryogels to completely fill a wound site, quickly control the hemorrhage, and provide stable mechanical properties under dynamic skin environment.

Invasion of pathogens due to skin loss is very destructive, and proper management needs to be seriously considered during wound healing. In this regard, the dressing materials with intrinsic antibacterial activity are highly compelling, as they could provide consistent bacterial inhibition without or minimally aided by antibiotics. Furthermore, recent studies showed that balancing oxidative stress is critical especially in healing of chronic wounds. Improper regulation of oxidative stress due to reactive oxygen species produced by metabolism would damage DNA and cause cellular malfunction. Accordingly, the scaffolds which possess antioxidant properties, like the compositions described herein, can solve this issue, and accelerate wound repair.

As a hydrolyzed derivative of collagen, gelatin is one of the key components of human and animal skin tissues. It is one of the most extensively studied natural biopolymers for wound healing, owing to its excellent biocompatibility, non-antigenicity, biodegradability, and a hemostatic effect. On the other hand, lignin is a plant derived natural polymer which traditionally is treated as a waste material. However, it has recently gained attention due to its remarkable biological features.

We describe herein multifunctional composite cryogels which possess a good antioxidant activity, a desirable antimicrobial performance, injectability and biodegradability. As is illustrated in FIG. 1, the cryogels were prepared by coherently mixing lignin microparticles with gelatin, and chemically crosslinking at subzero temperature. Preferably, the subfreezing exposure is for less than two days. With suitable formulation of these two materials, highly interconnected macroporus, stable cryogels were formed with a good swellability and improved mechanical properties. Addition of lignin also improved shape memory and injectability of the cryogel, and effectively inhibited colonization of both *Escherichia coli* (*E. Coli*) and *Staphylococcus aureus* (*S. Aureus*). Furthermore, the composite cryogels exhibited a good antioxidant property due to the presence of lignin.

Exemplary Preparation of Lignin-Gelatin Cryogels for Testing Purposes 0.1~1% (w./V) of lignin (bio-lignin, CIMV, Neuilly-sur-Seine, France) was added into 1 mM of NaOH aqueous solution, and kept in a sonication bath for 30 minutes. 6% (w/V) of Type A gelatin (Sigma-Aldrich, USA) was poured into solution followed by vigorous shaking on vortex mixer for a minute, and gently shaking in incubator at 37° C. for 30 minutes. Afterwards 0.05% of Glutaraldehyde (GA) was added into the solution under vortex shaking for 30 seconds, immediately poured into template, and then kept in a refrigerator/freezer at −20° C. for 24 hours. Finally, the cryogels were rinsed with warm deionized water for 4~5 times to remove GA and NaOH. As used herein, the names are expressed by combining "Gel" with lignin concentration. For example "Gel 0.1" refers to the composite cryogel initialized by the solution contains 0.1% (w./V) of lignin.

Physical and Chemical Characterization

Cryogel Micrograph and Pore Size Distribution.

Microstructure of porous cryogel network was analyzed using a Field emission scanning electron microscopy (FE-SEM, JEOL JSM 7600F, Tokyo, Japan). The dried cryogel samples were sputter-coated with platinum, and imaged at 5 kV. Based on the SEM image, Pore size distribution of the samples was calculated by "Image J" software. Pore sizes were measured from 50 different location if the image to obtain average size and standard deviation.

Swelling Test.

The swelling test was performed by immersing the cryogels into PBS for 24 hours, then completely drying them at 50° C. for 48 hours. Swelling ratio (Qm) was calculated by the following equation:

$$Qm = Ms/Md \qquad \text{(Equation 1)}$$

Where Ms is weight of the swollen sample, and Md is weight of the dried sample.

Determination of Pore Interconnectivity (PI).

Water-wicking method was applied to determine the pore interconnectivity of the cryogels. The fresh cryogels were weighed (Mf), then the water within interconnected pores was wicked away using Kimwipes and weighed again (Mw). Accordingly, the pore interconnectivity (PI) was calculated by the following equation:

$$PI = (Mf-Mw)/Mf \qquad \text{(Equation 2)}$$

FTIR.

Fourier transform infrared (FTIR) spectra of the composite cryogel and the individual polymers were collected using ATR-FTIR spectrometer (Thermo Fisher Scientific, USA). The data were recorded in 600-4000 cm$^{-1}$ of wavenumber range using Germanium substrate as a background.

Biodegradation.

The dried cryogels were weighed, dipped into phosphoric buffer saline (PBS) containing 0.05 mg/ml of collagenase, and maintained in an incubator at 37° C. After a period of time, buffer solution was removed from the samples, and the residues were washed away using dionized water and ethanol. Finally, the samples were dried again to measure the weight change. Similar experiments were also performed on PBS buffer without collagenase.

Compression Test.

The compression test for the cryogels was performed using Discovery Hybrid Rheometer (DHR-3, TA instrument, USA) operating in compression mode. The cylindrical cryogel with 13 mm of diameter and ~10 mm of height was placed between two parallel plates, then compressed with 0.1 mm/s of speed. Compression modulus of the samples was determined according to initial slope of the stress-strain curve.

Shape Recovery Rate.

The Shape recovery rate of the cryogels were tested during the compression. Initial height of the sample was determined at the force equal to zero. After compressing the samples up to 80% and 90%, the height was immediately returned back to the initial height. Then the height carefully lowered until the force becomes zero again. Finally, the shape recovery rate was calculated using the following equation:

$$SR = (Hf/Hi) \times 100\% \qquad \text{(Equation 2)}$$

Syringe Injectability Test.

A 2.5 ml syringe attached with a 16-gauge needle were used for the injectability test. Cylindrical cryogels with 4 mm of diameter and 1 mm of thickness were placed into the syringe loaded with ~0.5 ml of deionized water. Then, suspended in 0.2 mL of PBS. Next, these cryogels were syringe-injected using a 16-gauge needle. Briefly, cryogels were placed on the needle aperture and injected.

Antibacterial Activity Test

Antibacterial activities of the cryogels were tested by the agar diffusion method. Single colonies of *Escherichia coli* (*E. Coli*) and *Staphylococcus aureus* (*S. Aureus*) strains were isolated and cultured in Lysogeny broth (LB) media containing ampicillin (100 µg mL-1) at 37° C. overnight. Afterwards 200 µL of cultured strains were evenly diffused on the plate surface of LB-agar containing 100 µg/ml of ampicillin to get a mat of bacteria. Circular disks (~5 mm diameter) of the cryogels were attached on the top of bacteria strain in triplicate and incubated overnight.

Total Antioxidant Capacity Test

The total antioxidant capacity (TAOC) of the cryogels was determined by the Ferric Reducing Ability of Plasma (FRAP) assay, in which Fe$^{3+}$-tripyridyltriazine complex (TPTZ) is reduced to Fe2+ TPTZ. The assay kit was purchased from Beijing Solarbio Science & Technology Co., Ltd (Beijing, China), and measurement was conducted according to the manufacturer's instructions. Nanodrop 2000 (Thermo Fisher Scientific) was used to detect absorbance of mixture at 593 nm. FeSO$_4$ solution as a standard was prepared with different concentration in the range of 0.00156~0.4 µmole/ml to create a calibration curve. The TAOC data for the cryogels was expressed as µmole FeSO$_4$ equivalents.

Characterization of Lignin-Co-Gelatin Cryogels.

The pore size and architecture of lignin-co-gelatin cryogels were characterized by confocal microscopy (LSM800, Zeiss, Oberkochen, Germany). First, the cryogels were mounted on glass coverslip (#1) and hydrated with phosphate buffer saline (PBS, Sigma-Aldrich, St. Louis, Mo., USA). Then, the samples were imaged using the autofluorescence of lignin (excitation: 488 nm; emission: 535 nm) and collagen (excitation: 470 nm; emission: 520 nm). Pore sizes were evaluated using Fiji software and the analyze particle plugin. For each condition, one representative image was collected with a 1-µm separation between slices (z-stacks).

Results

Synthesis of Composite Cryogels

Figure 2:
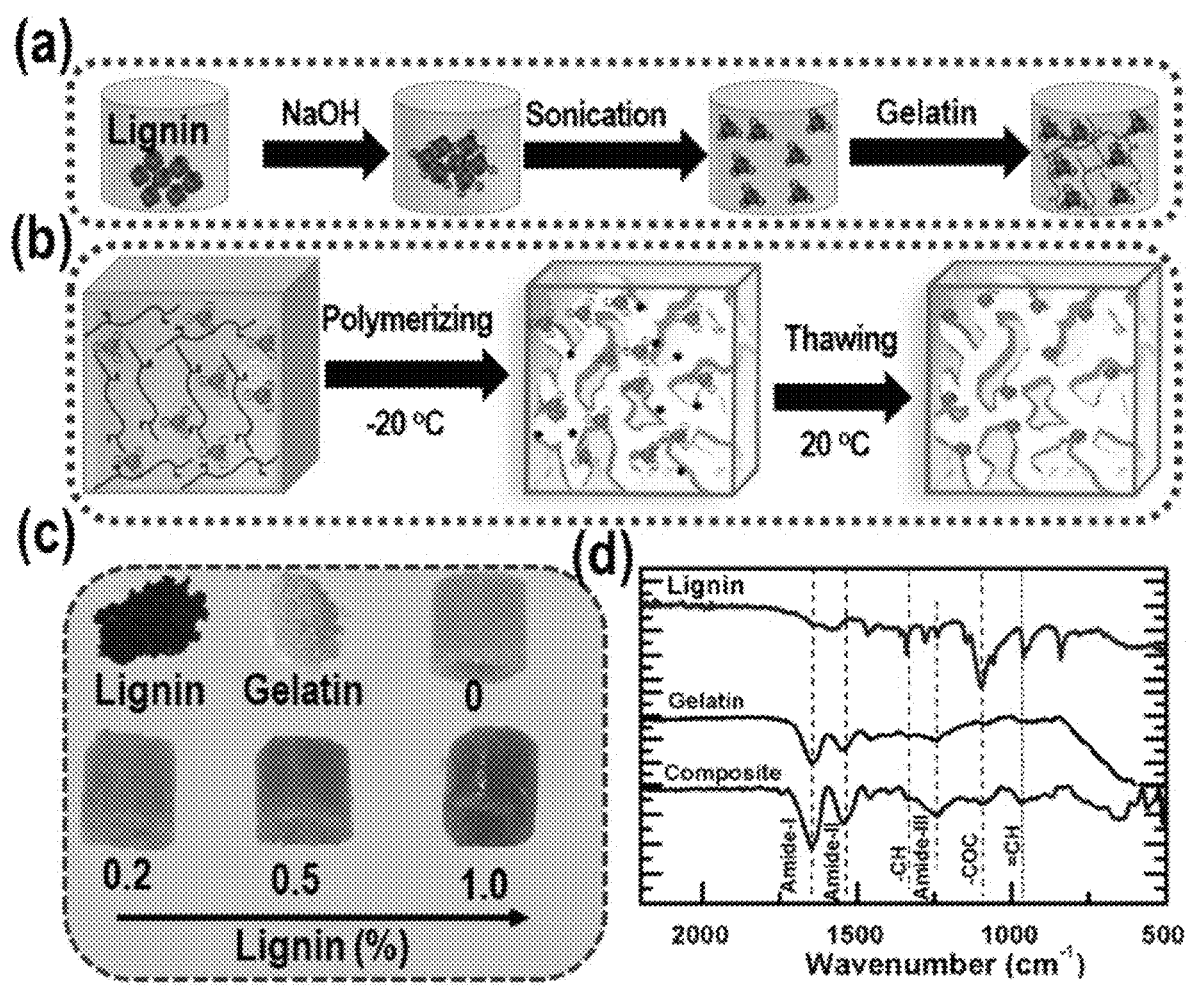
FIG. 2 is a multipanel display illustrating the fabrication of lignin-gelatin composite cryogels. Panel (a) is a schematic representation of the solution preparation, in which lignin dispersed into aqueous solution of gelatin using alkali-assisted ultra sonication. Panel (b) is a schematic presentation of the cryogel fabrication by using glutaraldehyde (GA) as a crosslinker, which is incorporated into the polymer walls of the cryogel during the chemical crosslinking process. Large pores remain after the frozen ice crystals thaw. Panel (c) includes several images of the prepared cryogels with different concentrations of lignin. Panel (d) presents FTIR spectra of composite cryogels and confirms the combined chemical structure of lignin and gelatin.

We successfully embedded lignin submicron particles into gelatin to produce multifunctional composite cryogels with excellent shape memory and injectability. Alkali assisted ultra-sonication technique was applied to disperse the lignin particles into the gelatin solution, in which hydroxide ions ($OH^-$) prevent the particle agglomeration (FIG. 2, Panel (a)). After we obtained homogenously mixed lignin-gelatin solution, cryogelation was performed at −20° C. using GA as a cross-linker (FIG. 2, panel (b)). The side views of the prepared cryogels was presented in FIG. 2, panel (c), in which pure gelatin cryogel shows a bright, yellow color. Incorporation of a dark, brown lignin into gelatin caused a clear color change in the cryogel, namely the cryogels became darken with increased amount of lignin. The chemical structure of the lignin-gelation composite cryogel was analyzed, according to FTIR spectra (FIG. 2, panel (d)). The absorption bands appeared at 1723 $cm^{-1}$ (C=O stretching), 1188 $cm^{-1}$ (C—O—C symmetric stretching), 1242 $cm^{-1}$ ($CH_3$ symmetric stretching) attribute to characteristics of gelatin in the composite cryogel. While absorption bands appeared at 1723 $cm^{-1}$ (C=O stretching), 1188 $cm^{-1}$ (C—O—C symmetric stretching), 1242 $cm^{-1}$ ($CH_3$ symmetric stretching) are corresponded to characteristics of lignin.

Cryogel Structure and Physiochemical Properties

Figure 3:
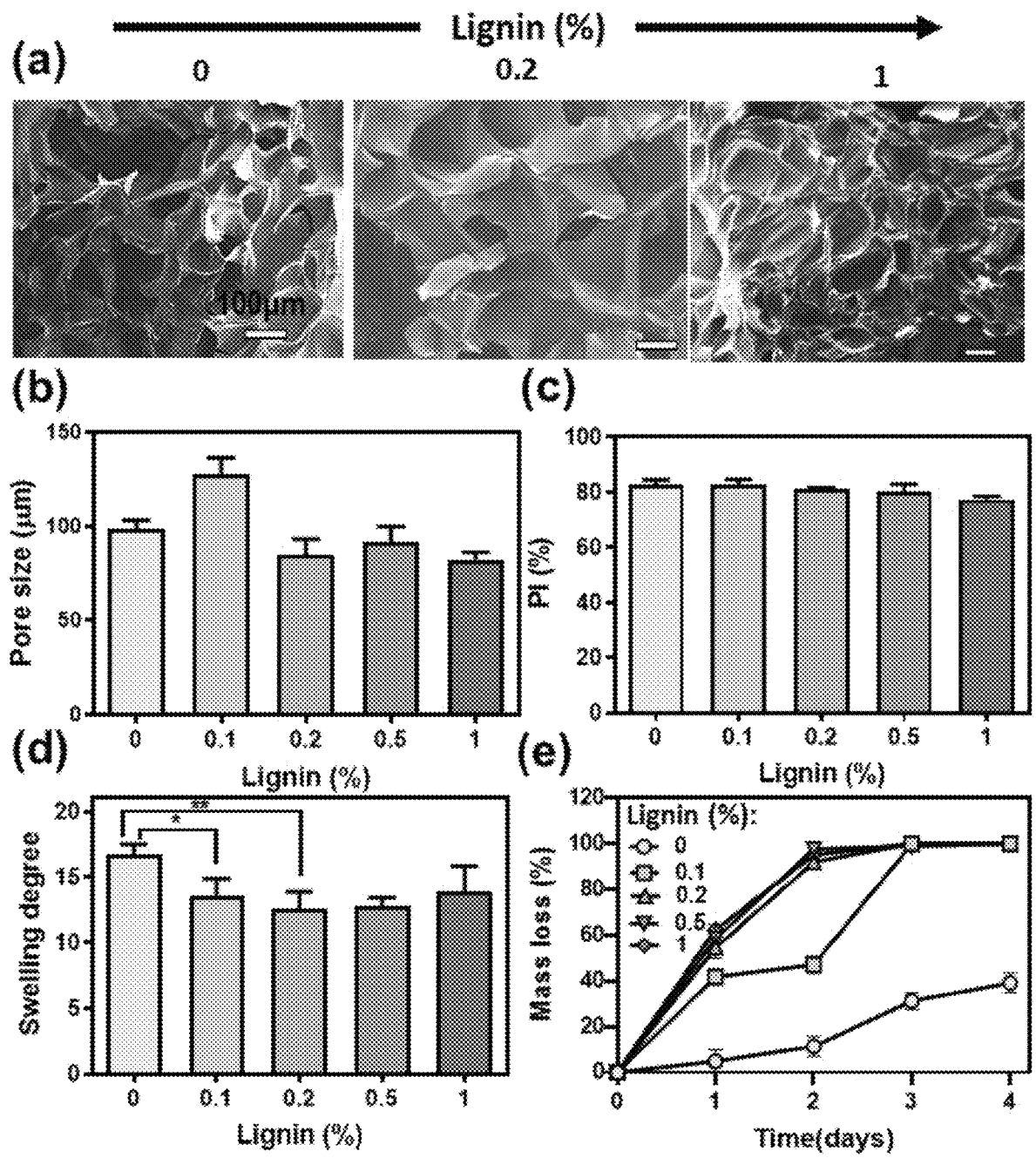
FIG. 3 is a multipanel display illustrating structural and physio-chemical properties of the composite cryogels. Panel (a) provides scanning electron microscopy (SEM) images. Panel (b) illustrates pore size distribution. Panel (c) shows pore interconnectivity of the cryogels and demonstrates their highly interconnected macroporus structure. Panel (d) shows the effect of lignin on swelling degree of the gelatin based cryogels. Panel (e) shows the biodegradation of the cryogels in PBS in the presence of collagenase (0.05 mg/ml) as a function of lignin concentration. $p<0.05$ (*), $p<0.01$(**).

Since maximum total polymer concentration in the initial solution is 7%, subzero temperatures allowed formation of large sized ice crystals which act as porogens. As a result, thawing of the cryogels in room temperature (RT) resulted in highly interconnected, macroporus polymeric network. Confocal microscopy images of cryogels demonstrated that all the cryogels could form highly interconnected macroporous structure, in which average pore sizes are in the range of 80~120 µm (FIG. 3, Panel (a) and Panel (b)). Among them, pure gelatin cryogel showed 100.4±7.7 µm of pore size, and pore size decrease is observed for the composite cryogels except the cryogel with 0.1% of lignin. This could be assigned to a thickened polymer wall caused by higher polymer concentration. Nevertheless, a high degree of pore interconnectivity in the cryogels was not significantly altered by the lignin concentration.

We analyzed effect of lignin incorporation on the swelling degree of the cryogels. The pristine gelatin cryogels showed 16.68±0.58 of the highest degree of swellability, and addition of lignin lowered the swelling ratio (FIG. 3, Pane (d)). This could be attributed to hydrophobic properties of lignin microparticles. The lowest swelling degree (12.6±0.91) was obtained for the composite cryogel with 0.2% lignin. This would result from a stronger intermolecular interaction between lignin and gelatin in this case, compared to other composite cryogels.

Further we examined biodegradation behavior of the cryogels in PBS buffer with and without adding collagenase. Without collagenase, any significant weight loss was not observed for all the cryogels. While addition of collagenase greatly accelerated the biodegradation rate, and interestingly incorporation of lignin strongly affected on the degradation of the cryogels. The cryogel without lignin exhibited about 40% of weight loss in 4 days. On the other hand, nearly complete weight loss was obtained for the composite cryogels in 2 days except the cryogel with 0.1% of lignin (FIG. 3, panel (e)), which completely disappeared in 3 days in the collagenase contained solution.

Figure 4:
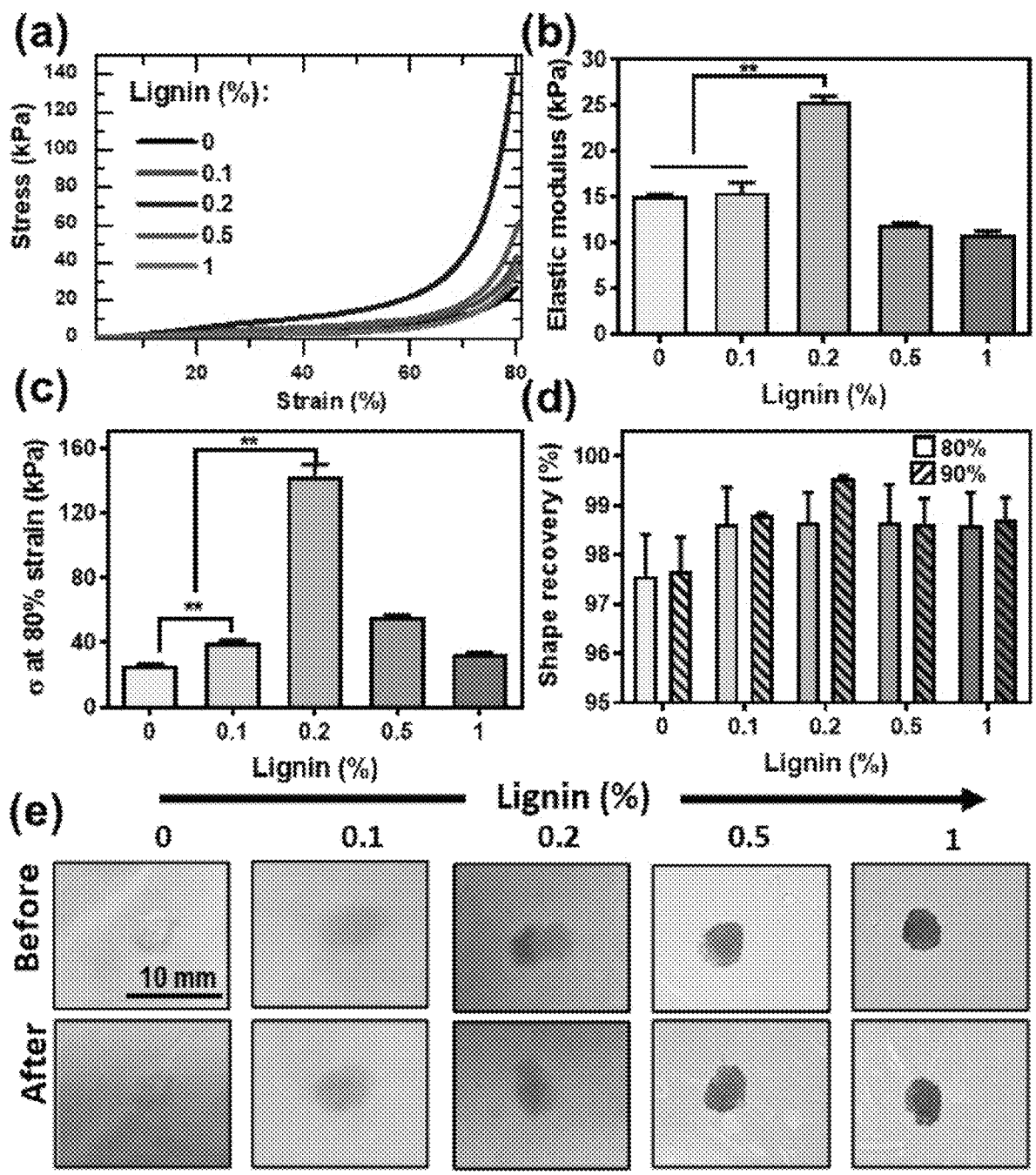
FIG. 4 is a multipanel display illustrating mechanical characteristics of the composite cryogels. Panel (a) presents a graph with the compressive stress-strain curves. Panel (b) is a bar graph showing the compressive elastic modulus of the cryogels. Panel (c) shows the stress required to compress the cryogels up to 80% of strain. Among the cryogels, the composite cryogel with 0.2% of lignin showed the best mechanical properties in terms of both elastic modulus and strength. Panel (d) shows the shape recovery rate of the cryogels after compressing up to 80 and 90%. In both cases, the cryogels showed above 95% of shape recovery. Panel (e) shows the shape of the cryogels before and after injection. The composite cryogels with lower concentration of lignin exhibit a better injectability. $p<0.05$ (*), $p<0.01$(**).

In order to examine the addition of lignin on mechanical properties and shape recovery rate of the gelatin based cryogel, we performed a compression test. As shown in FIG. 4 at panel a, "J" shaped strain-stress curves were obtained for all the cryogels, which can typically mimic to mechanical behavior of soft biological tissues. With references to FIG. 4, panels b-d, we determined compressive modulus of the cryogels using initial linear region of the curves (~20% of strain), and also compared their mechanical strength according to compression stress needed to yield higher strain (e.g.: 80%). In both cases, the composite cryogel with 0.2% of lignin showed the highest value (25 kPa of compressive modulus, and 140 kPa of stress at 80% of strain). These values are significantly higher compared to pure gelatin cryogel, for which 15 kPa of compressive moduli, and only 20 kPa of stress at 80% were observed. After the compression test, we released the stress to observe their shape recovery rate, as is shown in FIG. 4, at panel e. All the cryogels showed above 95% of shape recovery, even after compressing them up to 90% of their original height. Especially the composite cryogel with 0.2% of lignin exhibited 99.6±0.04% of shape recovery after 90% of compression, demonstrates its remarkable shape memory properties. Moreover we performed injectability test on the cryogels, and the composite cryogels with 0.1, 0.2% of lignin can be injected with a negligible shape loss. Whereas some shape loss was observed for pure gelatin cryogel and the composite cryogels with higher portion of lignin.

Antibacterial and Antioxidant Properties of the Cryogels

Figure 5:
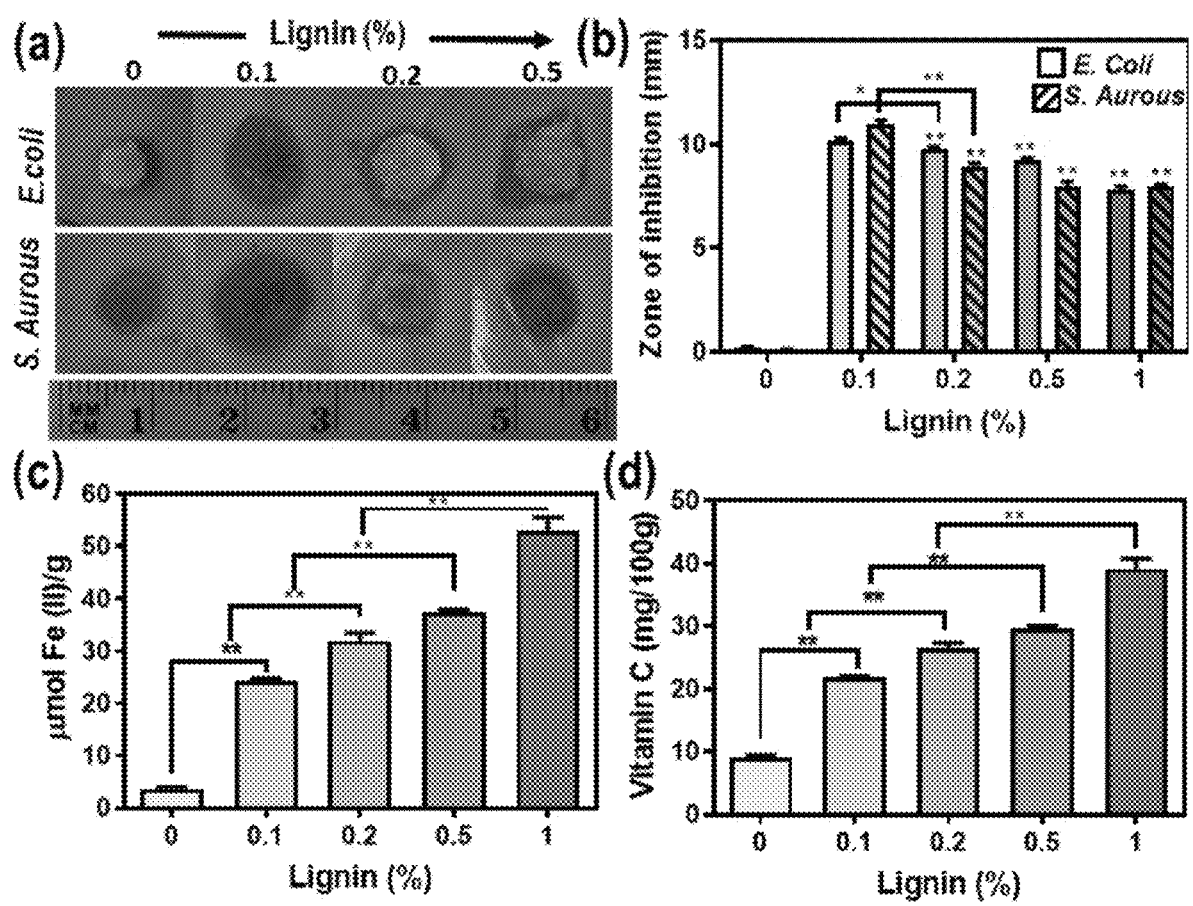
FIG. 5 is a multipanel display illustrating antimicrobial and antioxidant performance of the composite cryogels. Panel (a) shows the zone inhibition of the cryogels against *E. coli* and *S. aurous*, and Panel (b) shows zone diameters calculated according to a duplicate experiment with several measurements (n=5). The composite cryogels with 0.1 and 0.2% of lignin showed superior antimicrobial activity compared to those with higher concentrations of lignin. Panel (c) shows the ferric reducing ability of plasma (FRAP) value for the cryogels, based on their dry weights. Panel (d) shows the Vitamin C equivalent antioxidant activity of the cryogels based on their FRAP numerical correlation. Antioxidant activity of the cryogels is proportional to the lignin concentration, due to its natural antioxidant properties. $p<0.05$ (*), $p<0.01$(**).

Antibacterial activity of the cryogels were evaluated against gram-positive *S. Aureus* and gram_negative *E. Coli*, as they are most common sources of healthcare associated infection. As shown in FIG. 5, panels a-b, the pure gelatin cryogel didn't show any noticeable inhibition against these bacteria, whereas addition of lignin resulted in a clear inhibition effect against both *S. Aureus* and *E. Coli*. Interestingly the composite cryogels with 0.1% of lignin showed the highest antimicrobial activity amongst the composite cryogels. The antioxidant properties of cryogels examined using ferric reducing ability of plasma (FRAP) method, and obtained results compared with one of the commonly used antioxidants Vitamin C. As shown in FIG. 5, panels c-d, antioxidant activity of the cryogels is proportional to the lignin concentration, due to its natural antioxidant properties.

Combination with Other Treatment Agents

Figure 6:
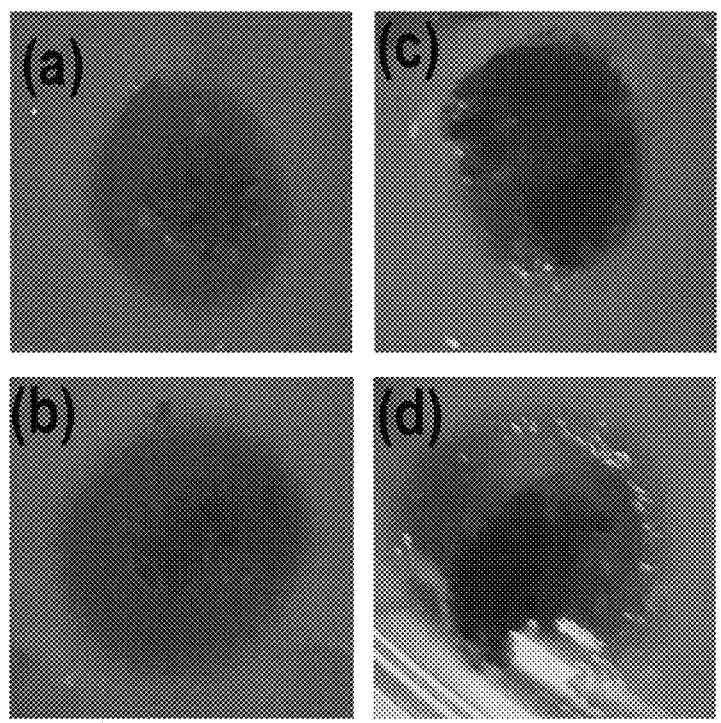
FIG. 6 shows the zone inhibition of the cryogels with 0.1% of lignin against *E. coli* and *S. aurous* without silver oxide (a and b), and with silver oxide (c and d).

Performance of the cryogels may be improved by combining them with other treatment agents such as copper oxide or silver oxide nanoparticles. This can be accomplished by combining the particles, at 0.0001~0.001 mole/liter, during formation of the gelation/lignin macroporous material. FIG. 6 shows the zone inhibition of the cryogels with 0.1% of lignin against *E. coli* and *S. aurous* without silver oxide (a and b), and with silver oxide (c and d), and it can be seen that while performance is good without the additive, it is improved on including the silver oxide particles.

The invention claimed is:
1. A method of preparing a macroporous composition for wound healing or tissue engineering, comprising:
dispersing lignin submicron particles within gelatin, the dispersing step forming a dispersion;

forming a cryogel from the dispersion by gelation of the dispersion at a subfreezing temperature, wherein said forming step crosslinks the gelatin while ice crystals are grown in the dispersion; and thawing the cryogel to room temperature to obtain the macroporous composition comprising crosslinked gelatin with the lignin submicron particles distributed therein.

2. The method of claim 1 wherein the cryogel comprises 0.1~1% (w/v) of the lignin submicron particles.

3. The method of claim 1 wherein the a cryogel comprises approximately 6% (w/v) of gelatin.

4. The method of claim 3 wherein the gelatin is an animal derived type A gelatin.

5. The method of claim 1 further comprising adding a crosslinking agent to the dispersion.

6. The method of claim 5 wherein the crosslinking agent is glutaraldehyde.

7. The method of claim 5 further comprising washing the microporous composition.

8. The method of claim 1 further comprising adding one or more of silver oxide or copper oxide nanoparticles to the dispersion, and wherein the one or more silver oxide or copper oxide nanoparticles are embedded in the microporous composition.

9. The method of claim 8 wherein the silver oxide or copper oxide nanoparticles are added to the dispersion at 0.0001~0.001 mole/liter.

10. The method of claim 1 wherein the microporous composition includes a plurality of pores ranging from 50 to 150 µm in size.

11. The method of claim 1 wherein the forming step takes place at the subfreezing temperature for less than two days.

12. A cryogel, comprising:

a macroporous composition of crosslinked gelatin; and lignin submicron particles distributed and embedded in the crosslinked gelatin, wherein the microporous composition includes a plurality of pores which are 50 to 150 µm in size, wherein the macroporous composition exhibits antioxidant activity, wherein the macroporous composition exhibits antibacterial activity, wherein the macroporous composition is dispensable from a syringe, wherein the macroporous composition is biodegradable in presence of collagenase, and wherein the microporous compositions recovers an original shape after compressing up to 90% of the original shape.

13. The cryogel of claim 12 further comprising copper oxide or silver oxide nanoparticles dispersed within the microporous composition.

* * * * *